United States Patent [19]

Heimke et al.

[11] Patent Number: 4,946,444
[45] Date of Patent: Aug. 7, 1990

[54] PERCUTANEOUS DEVICES WITH FLANGES OF VARIABLE STIFFNESS

[75] Inventors: Gunther Heimke, Clemson; Andreas F. von Recum, Six Mile, both of S.C.

[73] Assignee: Clemson University, Clemson, S.C.

[21] Appl. No.: 307,685

[22] Filed: Feb. 7, 1989

Related U.S. Application Data

[63] Continuation of Ser. No. 276,156, Nov. 23, 1988.

[51] Int. Cl.$^5$ ............................................. A61M 5/00
[52] U.S. Cl. ................................................... 604/175
[58] Field of Search .................. 604/174, 175, 8, 117, 604/278; 128/DIG. 26

[56] References Cited

U.S. PATENT DOCUMENTS 4,351,069  9/1982  Ballintyn et al. ............. 128/92 YQ
4,634,422  1/1987  Kantrowitz et al. .

OTHER PUBLICATIONS

W. L. Gore & Associates, Inc., Peritoneal Catheter, 1983 ©.
Grosse-Siestrup et al., "Design Criteria for Percutaneous Devices," Journal of Bio-Medical Materials Research, vol. 18, pp. 357–382, (1984).

*Primary Examiner*—C. Fred Rosenbaum
*Assistant Examiner*—Denise W. DeFranco
*Attorney, Agent, or Firm*—Dority & Manning

[57] ABSTRACT

A percutaneous implant device includes a main body portion and a flange extending outwardly from the main body portion. The flange has a free edge and can have a thickness that decreases as an imaginary point moves toward the free edge. The stiffness of the flange decreases as an imaginary point proceeds from portions of the flange nearest the main body portion to portions of the flange nearest the free edge. This is accomplished in one embodiment by a flange density that decreases as the imaginary point moves toward the free edge. In another embodiment, the porosity of the flange can increase as the imaginary point moves toward the free edge. The thickness and density of the flange can decrease while the porosity increases as the imaginary point moves toward the free edge. The thickness and thread count of a textile flange can decrease as the imaginary point moves toward the free edge. The thickness and packing density of a fibrous flange can decrease as the imaginary point moves toward the free edge.

9 Claims, 4 Drawing Sheets

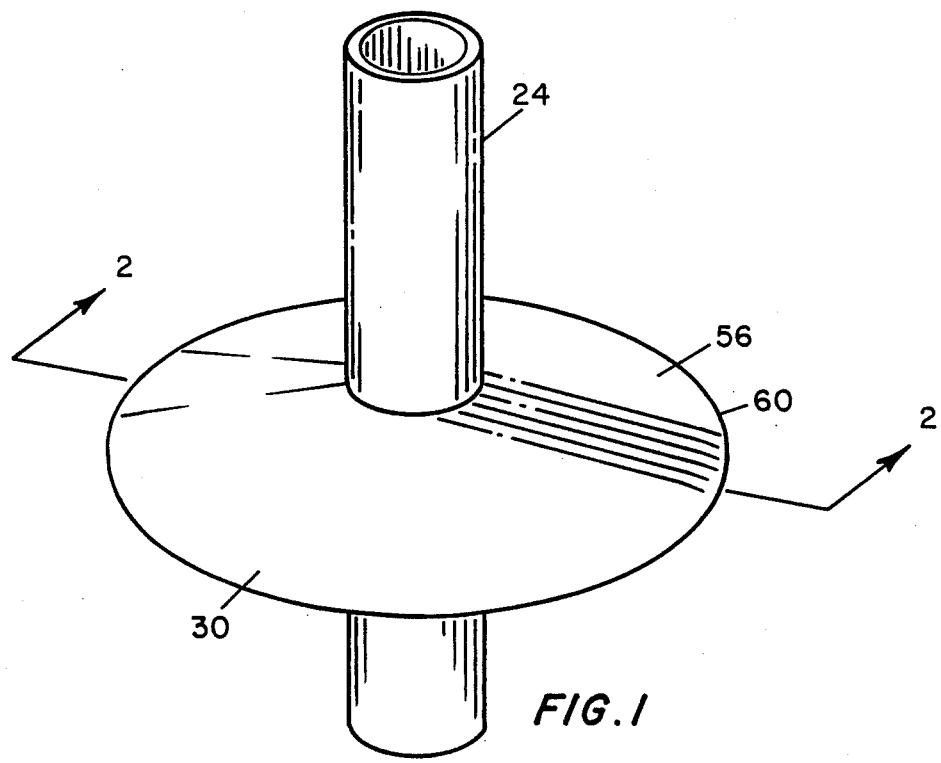
FIG.1
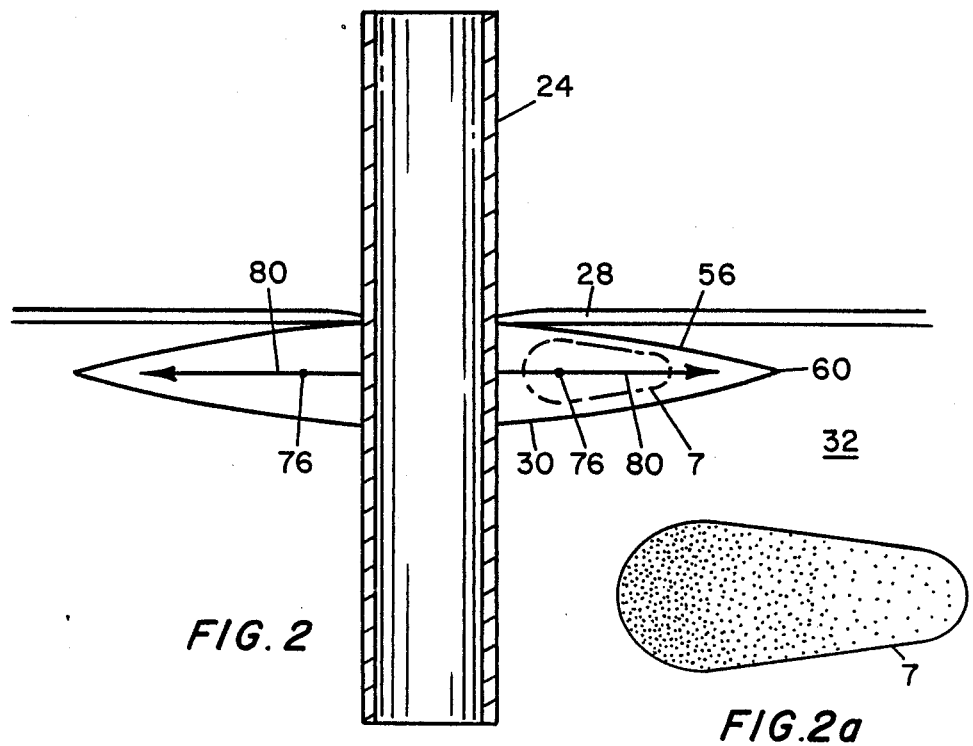
FIG.2
FIG.2a

PERCUTANEOUS DEVICES WITH FLANGES OF VARIABLE STIFFNESS

This is a continuation application of Ser. No. 07/276,156, filed on Nov. 23, 1988.

BACKGROUND OF THE INVENTION

The present invention relates to implant devices and more particularly to percutaneous implant devices.

Early percutaneous devices consisted of a pipe inserted through a surgically created opening in the skin. A sufficiently bio-compatible pipe material permitted such devices to remain in situ for a few weeks to a few months, as long as the devices were not mechanically loaded. However, the weight of conduits and wires passing through these pipes mechanically loaded the pipes. Mechanical loading also resulted from the movement of the patient and handling of the conduit and wires. Such mechanical loading caused stresses and strains along the interface between the percutaneous device and the body tissue. These stresses and strains irritated the tissue and caused local inflammation and tissue destruction. In time, severe epithelial down growth occurred, and the percutaneous device failed.

Early attempts to overcome this difficulty involved the use of particular coatings along the surface of the pipe. These attempts prolonged the useful life of the percutaneous device, but not to the degree necessary for patients needing dialysis or intravenous feeding for many years.

A later attempt to overcome this difficulty focused on the design of different flanges surrounding the pipe. The basic idea of these later attempts was to distribute the forces over a larger area of contact between the skin and the subcutaneous tissue on the one hand and the implant device on the other. Several such flange designs are mentioned and discussed in Grosse-Siestrup et al, "Design Criteria for Percutaneous Devices," Journal of Biomedical Materials Research, Volume 18, pp. 357–82 (1984). The basic thickness of the flanges shown in FIGS. 18–22, 24 and 25 is uniform, and the flanges are formed of a homogeneous material such as velour loops, woven or knitted structures, etc. (FIG. 22).

Another type of flange mentioned in Gross-Siestrup et al is shown in FIG. 26 and involves a polymer textile fabric, which is uniform in thickness and density. This textile fabric flange is not as stiff as the flanges discussed above and has a stiffness closer to that of the surrounding skin and subcutaneous tissue. However, the stiffness of these textile fabric flanges increases after tissue ingrowth and produces a stiffness discontinuity along the outside rim of these textile fabric flanges. Irritations of the tissue at the flange rim occurs and finally leads to failure of these subcutaneous implants.

U.S. Pat. No. 4,634,422 to Kantrowitz et al discloses a percutaneous access device (FIGS. 6 and 7) with a flange having a peripheral section of reduced uniform thickness, and flanges having a thickness which gradually decreases as one moves radially outwardly from the conduit to the free edge are also known.

OBJECTS AND SUMMARY OF THE INVENTION

It is the principal object of the present invention to eliminate the irritation at the interface between the percutaneous device and the surrounding skin and tissue to increase the useful life of the device for a period of time on the order of several years.

A further principal object of the present invention is to provide a percutaneous device with a flange having decreasing stiffness from the center to the free edge of the flange.

It is a yet further object of the present invention to provide a percutaneous device with a flange having a density that gradually decreases as one proceeds radially outwardly from the vicinity of the lead-through to the free edge of the flange.

It is another principal object of the present invention to provide a percutaneous device with a flange having a porosity that gradually increases as one proceeds radially outwardly from the vicinity of the lead-through to the free edge of the flange.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the percutaneous device of the present invention comprises a main body portion that surrounds a conduit. A flange surrounds the main body portion and extends therefrom to a free edge. The thickness of the flange may be uniform or it may decrease linearly as one approaches the free edge from the main body portion. In accordance with the invention, the stiffness of the flange is varied as a function of position on the flange. The stiffness is varied so as to decrease as an imaginary point moves in a direction going from the main body portion to a free edge of the flange. Preferably, the stiffness decreases linearly as this imaginary point moves in the direction from the main body portion to the free edge. The decreasing stiffness preferably is accomplished by gradually decreasing the density of the flange as the imaginary point moves from the main body portion to the free edge. Alternatively, the stiffness can be varied by providing a plurality of pores in the flange such that the volume of space occupied by the pores increases as the imaginary point moves in the direction from the main body portion to the free edge. In a textile flange, the number of threads per square inch can be decreased as the imaginary point moves in the direction from the main body portion to the free edge. In a flange formed of packed fibers, the packing density of the fibers decreases as the imaginary point moves in the direction from the main body portion to the free edge. Preferably, the stiffness changes linearly as a function of the position in the flange as an imaginary point moves in the direction from the main body portion to the free edge of the flange. In addition, the variable stiffness can be achieved by providing an increasing volume of pores in a flange formed of material of variable density.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 1 shows a perspective view of a device according to the present invention;

FIG. 2 illustrates a cross-section of the device of FIG. 1 implanted in a living host;

FIG. 2a illustrates an expanded view of a schematic cross-section taken from an embodiment such as shown in FIG. 2 for example.

DETAILED DESCRIPTION OF THE PREFERRED EMBODIMENTS

Reference now will be made in detail to the present preferred embodiments of the present invention, examples of which are illustrated in the accompanying drawings.

A preferred embodiment of the pharmaceutically protected percutaneous implant device of the present invention is shown in FIG. 1 for example and is represented generally by the numeral 20.

Figure 3:
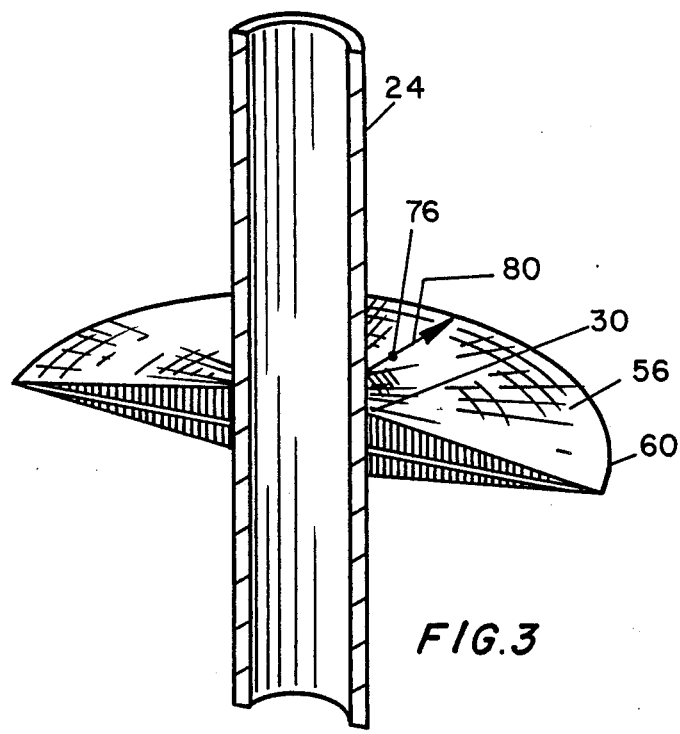
FIG. 3 illustrates a perspective cut away view of an alternative embodiment of the present invention.
Figure 4:
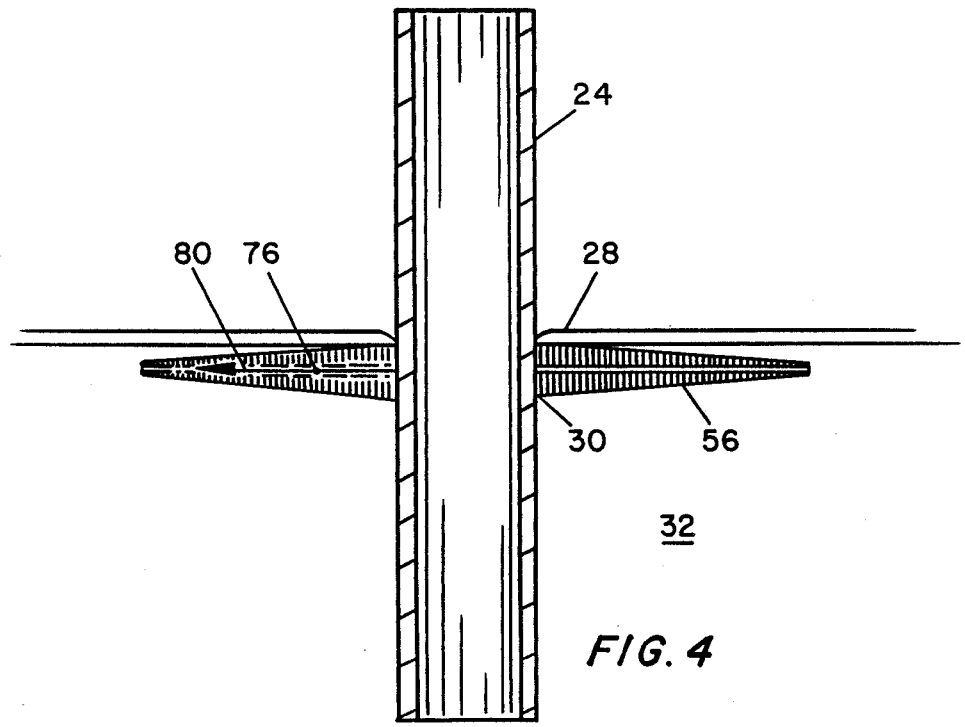
FIG. 4 illustrates a cross-sectional view of the device in FIG. 3 implanted in a living host.
Figure 5:
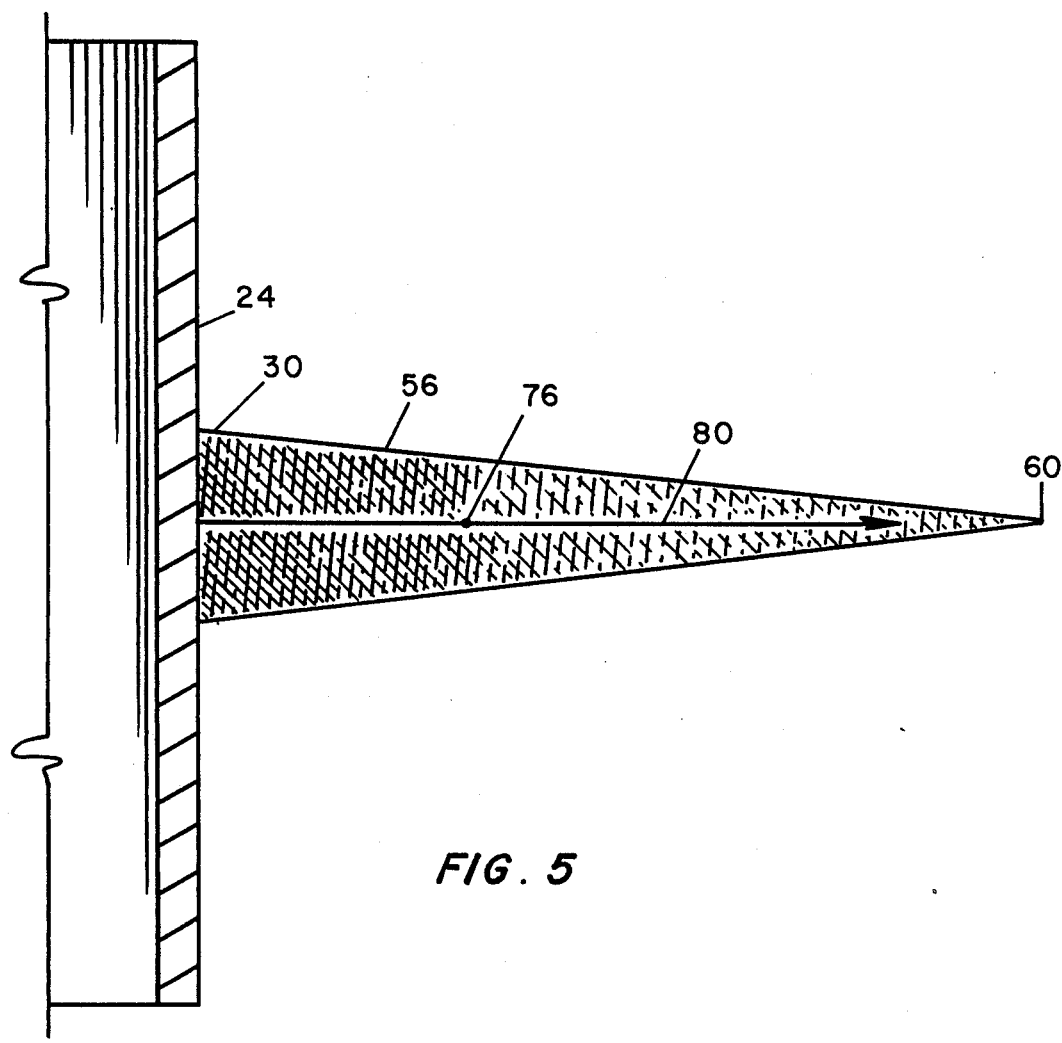
FIG. 5 illustrates a partial cross-sectional view of an alternative embodiment of the present invention.
Figure 6:
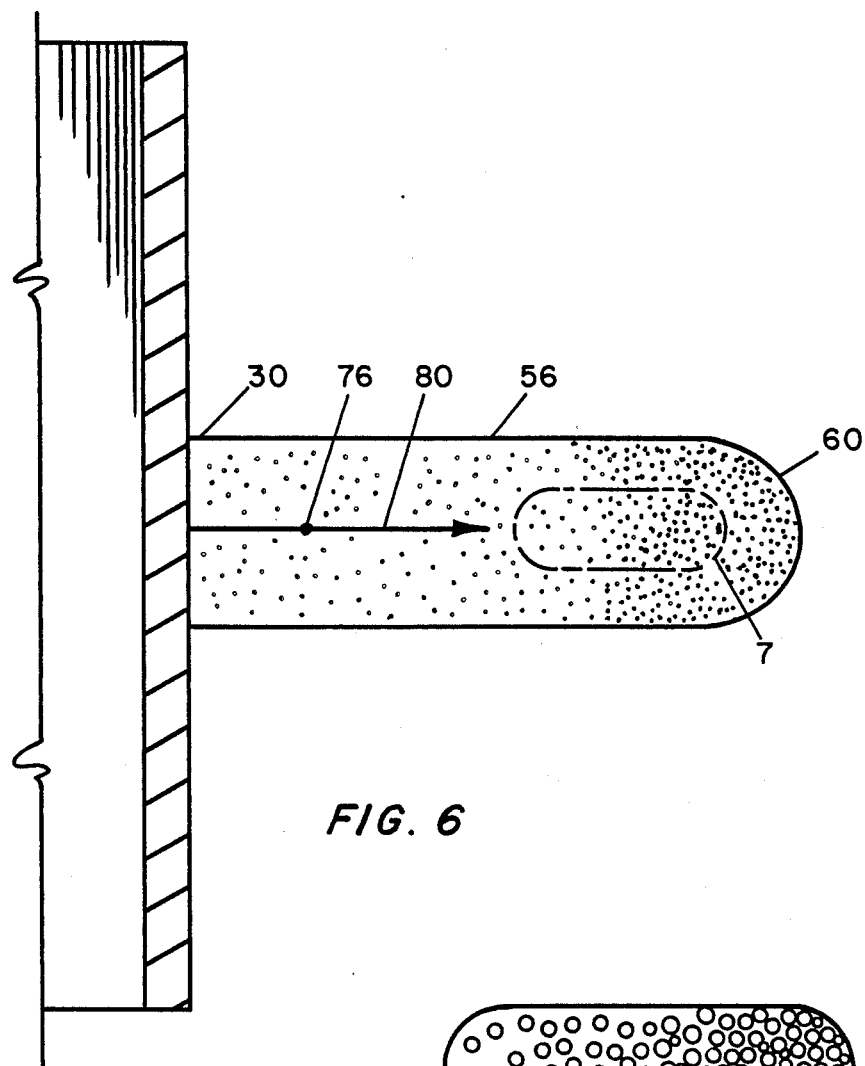
FIG. 6 illustrates a cross-sectional view of another alternative embodiment of the present invention.

The percutaneous device of the present invention includes a conduit for leading through the skin of a living human being or animal. As embodied herein and shown for example in FIGS. 2 and 4, a conduit 24 extends through an opening through skin 28 in a living human being or animal. Conduit 24 comprises a tube or pipe that also passes through the body's subcutaneous tissue 32. Conduit 24 preferably is formed of a bio-compatible material such as silicon, titanium, polycarbonate, etc. Preferably, only the tissue interfacing surface of the conduit need be formed of a bio-compatible material. Accordingly, various composite structures are suitable as conduits for purposes of the present invention.

The device of the present invention further includes a main body portion. As embodied herein and shown in FIGS. 1-6 for example, a main body portion 30 is integral with or in contact with the exterior wall of conduit 24.

In further accordance with the present invention, a flange extends outwardly from the main body portion and has a free edge. As embodied herein and shown in FIGS. 1-6 for example, a flange 56 extends radially outwardly from main body portion 30 and terminates in a free edge 60. Flange 56 preferably surrounds main body portion 30 and extends radially outwardly therefrom. Main body portion 30 can be integral with flange 56, as desired.

Figure 7:
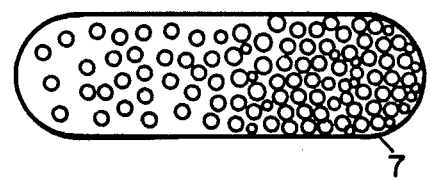
FIG. 7 illustrates an expanded view of a schematic cross-section taken from an embodiment such as shown in FIG. 6 for example.

In further accordance with the present invention, means are provided for varying the stiffness of different portions of the flange so that the stiffness decreases as an imaginary point proceeds from portions of the flange nearest the main body portion to portions of the flange nearest the free edge. As embodied herein and shown in FIGS. 2-6, the stiffness of flange 56 preferably decreases gradually as an imaginary point 76 moves in the direction of arrow 80 from the portion of flange 56 contacting conduit 24 to free edge 60. As embodied herein and shown in FIG. 2 for example, the stiffness varying means in a flange having a linearly decreasing thickness preferably includes a decreasing density of the flange as the imaginary point moves from the main body portion to the free edge. As shown in FIG. 2a for example, the density decreases as one proceeds from left to right, which corresponds to movement from the vicinity of conduit 24 toward free edge 60. This decreasing density results in a decreasing stiffness of the flange. In an alternative embodiment shown in FIGS. 6 and 7 for example, flange 56 can have a uniform thickness and the stiffness varying means preferably includes a plurality of pores wherein the volumetric density of the pores increases as an imaginary point moves from the portion of flange 56 contacting conduit 24 to free edge 60. As shown for flanges formed of fabric in FIGS. 3 and 4 for example, the stiffness varying means preferably includes decreasing thread counts as an imaginary point 76 proceeds from the main body portion toward free edge 60 of the flange. In other words, the number of individual thread strands per square inch of flange decreases as an imaginary point moves from conduit 24 to free edge 60. As shown in flanges formed of felt-like fibrous materials in FIG. 5 for example, the stiffness varying means preferably includes a decreasing packing density of fibers. The stiffness varying means of the flange also can include a combination of some of the foregoing structural techniques, such as for example an increasing porosity within a tapered flange of decreasing density.

As shown schematically by the presence of ever decreasing numbers of specs of shading in FIG. 2a for example, the stiffness can be preferably decreased by linearly decreasing the density of a flange as one proceeds from the main body portion to the free edge. As represented schematically in FIG. 7 for example, alternatively, the stiffness of a flange of uniform thickness can be decreased by linearly increasing the number or size of pores as one proceeds from the main body portion to the free edge.

As an imaginary point moves through the flange, it encounters different densities of the material forming the flange. Thus, the local density changes as a function of the position of the point within the flange. The combination of the individual local density characteristics constitutes a density profile for the flange. Similarly, if one provides the material forming the flange with a plurality of pores, one can use the porosity characterizing different local positions within the flange to obtain a porosity profile. In the present invention, the porosity profile is such that the volume of space occupied by the pores increases, preferably linearly, as an imaginary point moves from nearest the main body portion to the free edge. This can be accomplished by an increasing number of pores or an increase in the size of individual pores, or both.

Each of main body portion 30 and flange 56 preferably is formed of one or more of the following materials: silicone rubber, polytetrafluoroethylene, acrylic copolymers cast on polymeric substrates such as VERSA-POR manufactured by Gelman Sciences of Ann Arbor, Michigan, polysulfone, polyurethanes, polyethylene, and nylon. Such materials can be formed with varying densities and porosities according to known techniques, and these densities and porosities can be controlled to optimize them for a preselected degree of stiffness and a desired flexibility characteristic.

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. A percutaneous device comprising:
   (a) a main body portion, including means for receiving a percutaneous structure therein;
   (b) a flange extending outwardly from said main body portion and having a free edge;
   (c) means for varying the stiffness of different portions of said flange, said stiffness gradually decreasing as an imaginary point proceeds from portions of said flange nearest said main body portion to portions of said flange nearest said free edge; and
   (d) wherein, said stiffness varying means includes a plurality of pores defined in said flange, the volume of space occupied by said pores gradually increasing as said imaginary point moves from nearest said main body portion to said free edge.

2. A device as in claim 1, wherein:
   said volume of space occupied by said pores increases linearly as said imaginary point moves from nearest said main body portion to said free edge.

3. A percutaneous device comprising:
   (a) a main body portion, including means for receiving a percutaneous structure therein;
   (b) a flange surrounding said main body portion and having a free edge, said flange extending radially from said main body portion to said free edge and including a flange thickness decreasing as said imaginary point moves from said main body portion to said free edge;
   (c) means for varying the stiffness of said flange as a function of the radial position of an imaginary point in said flange, said stiffness decreasing as said imaginary point moves from nearest said main body portion to said free edge; and
   (d) wherein, said stiffness varying means includes a density profile defined in said flange, said density profile decreasing as said imaginary point moves from nearest said main body portion to said free edge.

4. A device as in claim 3, wherein:
   said density profile decreases linearly as said imaginary point moves from nearest said main body portion to said free edge.

5. A device as in claim 4, wherein:
   said flange thickness decreases linearly as said imaginary point moves from nearest said main body portion to said free edge.

6. A percutaneous device comprising:
   (a) a main body portion, including means for receiving a percutaneous structure therein;
   (b) a flange extending outwardly from said main body portion and having a free edge, said flange comprising a plurality of threads;
   (c) means for varying the stiffness of different portions of said flange, said stiffness decreasing as an imaginary point proceeds from portions of said flange nearest said main body portion to portions of said flange nearest said free edge; and
   (d) wherein, said stiffness varying means includes a thread count decreasing as an imaginary point moves from nearest said main body portion to said free edge.

7. A device as in claim 6, wherein:
   said thread count decreases linearly as said imaginary point moves from nearest said main body portion to said free edge.

8. A percutaneous device comprising:
   (a) a main body portion, including means for receiving a percutaneous structure therein;
   (b) a flange surrounding said main body portion and having a free edge, said flange extending radially from said main body portion to said free edge, said flange comprising a plurality of fibers;
   (c) means for varying the stiffness of said flange as a function of the radial position of an imaginary point in said flange, said stiffness decreasing as said imaginary point moves from nearest said main body portion to said free edge; and
   (d) wherein, said stiffness decreasing as said imaginary point moves from nearest said main body portion to said free edge; and
   (d) wherein, said stiffness varying means includes a decreasing packing density of fibers forming said flange as said imaginary point moves from nearest said main body portion to said free edge.

9. A device as in claim 8, wherein:
   said fiber packing density decreases linearly as said imaginary point moves from nearest said main body portion to said free edge.

* * * * *